United States Patent
Yamada et al.

(10) Patent No.: US 8,173,702 B2
(45) Date of Patent: May 8, 2012

(54) PESTICIDAL COMPOSITION AND METHOD FOR CONTROLLING HARMFUL INSECTS

(75) Inventors: Masahiro Yamada, Toyonaka (JP); Yoshito Tanaka, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 164 days.

(21) Appl. No.: 12/593,821

(22) PCT Filed: Mar. 27, 2007

(86) PCT No.: PCT/JP2008/056637
§ 371 (c)(1),
(2), (4) Date: Sep. 29, 2009

(87) PCT Pub. No.: WO2008/123571
PCT Pub. Date: Oct. 16, 2008

(65) Prior Publication Data
US 2010/0130602 A1   May 27, 2010

(30) Foreign Application Priority Data
Mar. 30, 2007   (JP) .................................. 2007-091201

(51) Int. Cl.
*A01N 37/34* (2006.01)
*A01N 25/00* (2006.01)
*A61K 31/275* (2006.01)

(52) U.S. Cl. .................. 514/520; 514/521; 424/405

(58) Field of Classification Search ................... None
See application file for complete search history.

(56) References Cited

U.S. PATENT DOCUMENTS
6,051,606 A   4/2000   Tanaka et al.

FOREIGN PATENT DOCUMENTS
EP   0 656 411 A1   6/1995
EP   0656411   *   6/1995
GB   2 150 026 A   6/1985

* cited by examiner

*Primary Examiner* — Alton Pryor
(74) *Attorney, Agent, or Firm* — Birch, Stewart, Kolasch & Birch, LLP

(57) ABSTRACT

A pesticidal composition containing: 4-methoxymethyl-2,3,5,6-tetrafluorobenzyl 3-(2-cyano-1-propenyl)-2,2-dimethyl-cyclopropanecarboxylate, a saturated hydrocarbon having an initial boiling point of 150° C. or higher and a 95%-distillation temperature of 300° C. or lower, and at least one alkyl carboxylate ester selected from the group consisting of the following esters (i) to (iii): (i) alkyl alkylcarboxylate esters having 12 to 20 carbon atoms, (ii) dialkyl dicarboxylate esters having 12 to 20 carbon atoms, and (iii) trialkyl acetylcitrate esters having 12 to 20 carbon atoms; has an excellent pesticidal activity.

13 Claims, No Drawings

PESTICIDAL COMPOSITION AND METHOD FOR CONTROLLING HARMFUL INSECTS

BACKGROUND OF THE INVENTION

1. Field of the Invention

The present invention relates to a pesticidal composition and a method for controlling harmful insects.

2. Description of the Prior Art

JP 2004-2363 A describes that 4-methoxymethyl-2,3,5,6-tetrafluorobenzyl 3-(2-cyano-1-propenyl)-2,2-dimethylcyclopropanecarboxylate has a pesticidal activity, and JP-2004-2363 A describes compositions containing the compound, dichloromethane and kerosene in its Preparative Examples and Examples.

SUMMARY OF THE INVENTION

An object of the present invention is to provide a pesticidal composition having an excellent pesticidal activity and a method for controlling harmful insects.

After intensive studies to find a pesticidal composition having an excellent pesticidal activity and a method for controlling harmful insects, the inventor has found that a pesticidal composition, which contains 4-methoxymethyl-2,3,5,6-tetrafluorobenzyl 3-(2-cyano-1-propenyl)-2,2-dimethylcyclopropanecarboxylate, a saturated hydrocarbon having an initial boiling point of 150° C. or higher and a 95%-distillation temperature of 300° C. or lower, and at least one glycol ether selected from the group consisting of monoalkylene glycol monoalkyl ethers and dialkylene glycol monoalkyl ethers, has an excellent pesticidal activity, and achieved the present invention.

The present invention provides:

1. A pesticidal composition, comprising: 4-methoxymethyl-2,3,5,6-tetrafluorobenzyl 3-(2-cyano-1-propenyl)-2,2-dimethylcyclopropanecarboxylate; a saturated hydrocarbon having an initial boiling point of 150° C. or higher and a 95%-distillation temperature of 300° C. or lower; and at least one glycol ether selected from the group consisting of monoalkylene glycol monoalkyl ethers and dialkylene glycol monoalkyl ethers;

2. The pesticidal composition as described in 1, wherein the composition comprises the saturated hydrocarbon in an amount of 0.5 to 10 parts by weight per part by weight of the glycol ether;

3. The pesticidal composition as described in 1 or 2, wherein the composition comprises 4-methoxymethyl-2,3,5,6-tetrafluorobenzyl 3-(2-cyano-1-propenyl)-2,2-dimethylcyclopropanecarboxylate in an amount of 0.00001 to 0.1 part by weight per part by weight of the glycol ether;

4. The pesticidal composition as described in any one of 1 to 3, wherein the composition comprises 4-methoxymethyl-2,3,5,6-tetrafluorobenzyl 3-(2-cyano-1-propenyl)-2,2-dimethylcyclopropanecarboxylate in an amount of 0.0001 to 0.5% by weight;

5. The pesticidal composition as described in any one of 1 to 4, wherein the glycol ether is one or two glycol ethers selected from the group consisting of mono-($C_2$-$C_3$)-alkylene glycol mono-($C_1$-$C_3$)alkyl ethers and di-($C_2$-$C_3$)-alkylene glycol mono-($C_1$-$C_3$)-alkyl ethers;

6. The pesticidal composition as described in any one of 1 to 4, wherein the glycol ether is one or two glycol ethers selected from the group consisting of propylene glycol monomethyl ether and propylene glycol monoethyl ether;

7. The pesticidal composition as described in any one of 1 to 6, wherein the composition is for controlling insects Blattaria;

8. A method for controlling harmful insect comprising applying an effective amount of a pesticidal composition comprising: 4-methoxymethyl-2,3,5,6-tetrafluorobenzyl 3-(2-cyano-1-propenyl)-2,2-dimethylcyclopropanecarboxylate; a saturated hydrocarbon having an initial boiling point of 150° C. or higher and a 95%-distillation temperature of 300° C. or lower; and at least one glycol ether selected from the group consisting of monoalkylene glycol monoalkyl ethers and dialkylene glycol monoalkyl ethers to the insect or a locus where the insects inhabits;

9. The method as described in 8, wherein the composition comprises the saturated hydrocarbon in an amount of 0.5 to 10 parts by weight per part by weight of the glycol ether;

10. The method as described in 8 or 9, wherein the composition comprises 4-methoxymethyl-2,3,5,6-tetrafluorobenzyl 3-(2-cyano-1-propenyl)-2,2-dimethylcyclopropanecarboxylate in an amount of 0.00001 to 0.1 part by weight per 1 part by weight of the glycol ether;

11. The method as described in any one of 8 to 10, wherein the composition comprises 4-methoxymethyl-2,3,5,6-tetrafluorobenzyl 3-(2-cyano-1-propenyl)-2,2-dimethylcyclopropanecarboxylate in an amount of 0.0001 to 0.5% by weight;

12. The method described in any one of 8 to 11, wherein the glycol ether is one or two glycol ethers selected from the group consisting of mono-($C_2$-$C_3$)-alkylene glycol mono-($C_1$-$C_3$)alkyl ethers and di-($C_2$-$C_3$)-alkylene glycol mono-($C_1$-$C_3$)-alkyl ethers;

13. The method described in any one of 8 to 11, wherein the glycol ether is one or two glycol ethers selected from the group consisting of propylene glycol monomethyl ether and propylene glycol monoethyl ether;

14. The method described in any one of 8 to 13, wherein the composition is for controlling insects Blattaria; and 15. A pest-controlling agent, comprising the pesticidal composition as described in any one of 1 to 7.

The pesticidal composition according to the present invention has an excellent pesticidal activity. The pest control method according to the present invention allows control of pests.

DETAILED DESCRIPTION OF THE INVENTION

A pesticidal composition according to the present invention (hereinafter, referred to as the inventive composition) contains 4-methoxymethyl-2,3,5,6-tetrafluorobenzyl 3-(2-cyano-1-propenyl)-2,2-dimethylcyclopropanecarboxylate, a saturated hydrocarbon and a glycol ether.

4-Methoxymethyl-2,3,5,6-tetrafluorobenzyl 3-(2-cyano-1-propenyl)-2,2-dimethylcyclopropanecarboxylate for use in the invention (hereinafter, referred to as the Ester compound) is a compound described, for example, in U.S. Pat. No. 6,908,945, and can be produced according to the method described therein.

The Ester compound has isomers attributable to the two asymmetric carbon atoms present in the cyclopropane ring and also has isomers derived from a double bond, but each isomer and a mixture of the isomers at any rate are also included in the Ester compound.

In the present invention, as the saturated hydrocarbons, various saturated hydrocarbon solvents having an initial boiling point of 150° C. or higher and a 95%-distillation temperature of 300° C. or lower (hereinafter, referred to as the Saturated Hydrocarbon) substantially containing at least one member selected from various saturated hydrocarbons (straight-chain saturated hydrocarbons, branched-chain saturated hydrocarbons, and alicyclic saturated hydrocarbons) can be used. Those having an initial boiling point of 150° C. or higher and a dry point of 300° C. or lower may also be used. Examples of the Saturated Hydrocarbon solvents include Isopar G (manufactured by Exxon Mobil Corp., initial boiling point: 160° C., dry point: 176° C.), Isopar L (manufactured by Exxon Mobil Corp., initial boiling point: 189° C., dry point: 207° C.), Isopar H (manufactured by Exxon Mobil Corp., initial boiling point: 178° C., dry point: 188° C.), Isopar M (manufactured by Exxon Mobil Corp., initial boiling point: 223° C., dry point: 254° C.), Norpar 13 (manufactured by Exxon Mobil Corp., initial boiling point: 222° C., dry point: 242° C.), Norpar 15 (manufactured by Exxon Mobil Corp., initial boiling point: 249° C., dry point: 274° C.), Exxsol D40 (manufactured by Exxon Mobil Corp., initial boiling point: 164° C., dry point: 192° C.), Exxsol D60 (manufactured by Exxon Mobil Corp., initial boiling point: 187° C., dry point: 209° C.), Exxsol D80 (manufactured by Exxon Mobil Corp., initial boiling point: 208° C., dry point: 243° C.), Neochiozol (manufactured by Chuokasei Co., Ltd., initial boiling point: 225° C., dry point: 247° C.), IP solvent 2028 (manufactured by Idemitsu Kosan Co., Ltd., initial boiling point: 213° C., 95%-distillation temperature: 250° C.) and kerosene.

The glycol ether for use in the invention is, for example, monoalkylene glycol monoalkyl ether or dialkylene glycol monoalkyl ether (hereinafter, referred to as the Glycol Ether), and specifically mono-($C_2$-$C_3$)-alkylene glycol mono-($C_1$-$C_3$)-alkyl ether or di-($C_2$-$C_3$)-alkylene glycol mono-($C_1$-$C_3$)-alkyl ether. Typical examples thereof include ethylene glycol monomethyl ether, ethylene glycol monoethyl ether, ethylene glycol monopropyl ether, diethylene glycol monomethyl ether, diethylene glycol monoethyl ether, diethylene glycol monopropyl ether, propylene glycol monomethyl ether, propylene glycol monoethyl ether, propylene glycol monopropyl ether, dipropylene glycol monomethyl ether, dipropylene glycol monoethyl ether, and dipropylene glycol monopropyl ether.

As for the amounts of the Saturated Hydrocarbon and the Glycol Ether, the inventive composition contains the Saturated Hydrocarbon usually in an amount of 0.5 to 10 parts by weight per part by weight of the Glycol Ether, and the inventive composition contains the Saturated Hydrocarbon and the Glycol Ether in a total amount of usually 90 to 99.999% by weight, preferably 95 to 99.999% by weight.

As for the amounts of the Ester compound and the Glycol Ether, the inventive composition contains the Ester compound usually in an amount of 0.00001 to 0.1 part by weight per part by weight of the Glycol Ether, and the Ester compound in an amount of usually 0.0001 to 0.5% by weight, preferably 0.001 to 0.5% by weight.

The inventive composition may contain, as needed, one or more of additional additives such as other insecticidally active ingredients, acaricidally active ingredients, repellently active ingredients, synergists, and flavoring agents.

Examples of the insecticidally active ingredients and acaricidally active ingredients include:
organic phosphorus compounds such as Fenitrothion, Fenthion, Diazinon, Chlorpyrifos, Acephate, Methidathion, Disulfoton, DDVP, Sulprofos, Cyanophos, Dioxabenzophos, Demethoate, Phenthoate, Malathion, Trichlorfon, Azinphosmethyl, Monocrotophos, Ethion, Dichlorvos, Profenofos, Sulprofos, Phenthoate, Isoxathion, Tetrachlorvinphos, Terbufos, Phorate, Chiorethoxyfos, Fosthiazate, Ethoprophos and Cadusafos; carbamate compounds such as BPMC, Benfuracarb, Propoxur, Carbosulfan, Carbaryl, Methomyl, Ethiofencarb, Aldicarb, Oxamyl, Fenothiocarb, Thiodicarb, Alanycarb, Methiocarb and Cartap; pyrethroid compounds such as Etofenprox, Fenvalerate, Esfenvalerate, Fenpropathrin, Cycloprothrin, Fluvalinate, tau-Fluvalinate, Bifenthrin, Halfenprox, Tralomethrin, Silafluofen, d-Resmethrin, Acrinathrin, Tefluthrin, Transfluthrin, Tetramethrin, Allethrin, d-Furamethrin, Prallethrin, Empenthrin, Flucythrinate, Flumethrin, and 5-(2-propynyl)furfuryl 2,2,3,3-tetramethylcyclopropanecarboxylate;

Acetamiprid, Nitenpyram, Thiacloprid, Thiamethoxam, Dinotefuran, Clothianidin, Imidacloprid, etc; chlorinated hydrocarbon compounds such as Endosulfan, γ-BHC, and 1,1-bis(chlorophenyl)-2,2,2-trichloroethanol; benzoylphenyl urea compounds such as Chlorfluazuron, Teflubenzuron, Fulfenoxlon, Lufenuron, Hexaflumuron, Diflubenzuron, Triflumuron, Fluazuron, Novaluron, Triazuron and Bistrifluron; phenylpyrazole compounds such as Acetoprole, Pyriprole, Pyrafluprole and Ethiprole;

benzoylhydrazine compounds such as Tebufenozide, Chromafenozide, Methoxyfenozide and Halofenozide; Metoxadiazone; Bromopropylate; Tetradifon; Chinomethionate; Pyridaben; Fenpyroximate; Diafenthiuron; Tebufenpyrad; Pymetrozine; Fronicamide; Triazamate; Buprofezin; Chlorfenapyr; Indoxacarb; Pyridalyl; Cyromazine; Fluacrypyrim; Etoxazole; Fenazaquin; Acequinocyl; Hexythiazox; Clofentezine; Fenbutatin oxide; Dicofol; Propargite; Amitraz; Bensultap; Thiocyclam; Spirodiclofen; Spiromesifen; Amidoflumet; Metaflumizone; Flubendiamide; Chlorantraniliprole; pyrifluquinazon; Polynactin complexes [tetranactin, dinactin and trinactin], Pyrimidifen; Milbemectin; Abamectin; Spinosad; Emamectin benzoate; Ivermectin; and Azadirachtin.

Examples of the repellently active ingredients include 3,4-caranediol, N,N-diethyl-m-toluamide, 1-methylpropyl 2-(2-hydroxyethyl)-1-piperidinecarboxylate, limonene, linalool, citronellal, menthol, menthane, hinokitiol, geraniol, eucalyptol, p-menthane-3,8-diol, and plant essential oils such as hyssop oil.

Examples of the synergists include bis-(2,3,3,3-tetrachloropropyl)ether [S-421], N-(2-ethylhexyl)bicyclo[2,2,1]hept-5-ene-2,3-dicarboxyimide [product name: MGK-264], α-[2-(2-butoxyethoxy)ethoxy]-4,5-methylenedioxy-2-propyltoluene[piperonyl butoxide], IBTA (Isobornyl thiocyanatoacetate) and N-(2-ethylhexyl)-1-isopropyl-4-methylbicyclo[2,2,2]-octa-5-ene-2,3-dicarboxyimide (product name: Synepirin 500).

Examples of the harmful insects that can be controlled with the inventive composition include arthropods such as insects and mites, and typical examples include the followings:

Lepidoptera: Pyralidae such as *Chilo suppressalis, Cnaphalocrocis medinalis*, and *Plodia interpunctella*; Noctuidae such as *Spodoptera litura, Pseudaletia separata*, and *Mamestra brassicae*; Pieridae such as *Pieris rapae crucivora*; ortricidae such as *Adoxophyes orana*; Carposinidae; Lyonetiidae; Lymantriidae; Antographa; *Agrotis* spp. such as *Agrotis segetum* and *Agrotis Ipsilon*; *Helicoverpa* spp.; *Heliothis* spp., *Plutella xylostella, Parnara guttata guttata, Tinea pellionella, Tineola bisselliella*, etc.

Diptera: *Culex* such as *Culex pipiens pallens, Culex tritaeniorhynchus* and *Culex quinquefasciatus; Aedes* such as *Aedes aegypti* and *Aedes albopictus*; Anophelinae such as *Anopheles sinensis* and *Anopheles gambiae*; Chironomidae; Muscidae such as *Musca domestics, Muscina stabulans*, and *Fannia canicularis*; Calliphoridae, Sarcophagidae; Anthomyiidae such as *Delia platura* and *Delia antiqua*; Tephritidae, Drosophilidae, Psychodidae, Phoridae, Tabanidae, Simuliidae, Culicoides, Ceratopogonidae, etc.

Blattaria: *Blattella germanica, Periplaneta fuliginosa, Periplaneta americana, Periplaneta brunnea, Lobopterella dimidiatipes*, etc.

Hymenoptera: Formicidae, Vespidae, Bethylidae, Tenthredinidae such as *Athalia rosae ruficornis*, etc.

Siphonaptera: *Ctenocephalides canis, Ctenocephalides felis felis, Pulex irritans*, etc.

Anoplura: *Pediculus humanus, Pthirus pubis, Pediculus capitis, Pediculus humanus*, etc.

Isoptera (termites): *Reticulitermes speratus speratus, Coptotermes formosanus*, etc.

Hemiptera: Delphacidae such as *Laodelphax stratella, Nilaparvata lugens*, and *Sogatella furcifera*; Deltocephalidae such as *Nephotettix cincticeps* and *Nephotettix virescens*; Aphididae; Pentatomidae; Aleyrodidae; Coccoidae; Tingidae; Psyllidae; Cimicidae; etc.

Coleoptera: *Attagenus japonicus, Anthrenus verbasci*; corn rootworms such as Western corn rootworm and Southern corn rootworm; Scarabaeidae such as *Anomala cuprea* and *Anomala rufocuprea*; Curculionidae such as *Sitophilus zeamais, Lissorhoptrus oryzophilus, Anthonomus grandis grandis*, and *Callosobruchus chinensis*; Tenebrionidae such as *Tenebrio molitor* and *Tribolium castaneum*; Chrysomelidae such as *Oulema oryzae, Phyllotreta striolata*, and *Aulacophora femoralis*; Anobiidae, *Epilachna* spp. such as *Epilachna vigintioctopunctata*; Lyctidae; Bostrychidae; Cerambycidae; *Paederus fuscipes*; etc.

Thysanoptera (thrips): *Thrips palmi, Frankliniella occidentalis, Thrips hawaiiensis*, etc.

Orthoptera: Gryllotalpidae, Acrididae, etc.

Acarines: Pyroglyphidae such as *Dermatophagoides farinae* and *Dermatophagoides pteronyssinus*; Acaridae such as *Tyrophagus putrescentiae* and *Aleuroglyphus ovatus*; Glycyphagidae such as *Glycyphagidae privatus, Glycyphagidae domesticus*, and *Glycyphagus destructor*; Cheyletidae such as *Cheyletus malaccensis* and *Cheyletus fortis*; Tarsonemidae; Chortoglyphidae; Haplochthoniidae; Tetranychidae such as *Tetranychus urticae, Tetranychus Kanzawai, Panonychus citri*, and *Panonychus ulmi*; Ixodidae such as *Haemaphysalis longicornis*; etc.

The inventive composition is prepared, for example, by mixing and dissolving the Ester compound, the Saturated Hydrocarbon and the Glycol Ether, and as needed the other pesticidally active ingredient, acaricidally active ingredient, repellently active ingredient, synergist, flavoring agent and others, at room temperature or under heat.

When the inventive composition is used for pest control, the inventive composition may be applied as it is or formulated into the front of a pest-controlling agent preparation containing the inventive composition.

The formulations include, for example, oil, emulsion, water-dispersible powder, flowable agent (aqueous suspension, aqueous emulsion, etc.), powder, granule, aerosol, heated vaporization agent (insecticide coil, insect electrocuting matt, heated insecticide-vaporizing agent with liquid-absorbing shaft, etc.), heated fumigant (self-combustion fumigant, chemical-reaction fumigant, porous-ceramic-plate fumigant, etc.), unheated vaporization agent (resin vaporization agent, impregnated paper vaporization agent, etc.), spraying agent (fogging, etc.), ULV agent, and poisonous bait.

These formulations are produced, for example, by the following methods.

(1) Method of mixing the inventive composition with a solid carrier, liquid carrier, gas carrier, bait or the like, and additionally other auxiliaries for formulation such as a surfactant if needed, and processing the resultant mixture;

(2) Method of impregnating a base material with the inventive composition; and (3) Method of mixing the inventive composition with a base material and molding the mixture.

The inventive composition is usually incorporated into a total amount of 0.1 to 95% by weight in these formulations, although the content may vary depending on the form of the formulation.

Examples of the solid carriers used for formulation include clays (kaolin clay, diatomaceous earth, synthetic hydrated silicon oxide, bentonite, Fubasami clay, acid clay, etc.), talcs, ceramics, other inorganic minerals (sericite, quartz, sulfur, activated carbon, calcium carbonate, Hydration silica, montmorillonite, etc.), and chemical fertilizers (ammonium sulfate, ammonium phosphate, ammonium nitrate, urea, ammonium chloride, etc.). Examples of the liquid carriers include water, alcohols (methanol, ethanol, etc.), ketones (acetone, methylethylketone, etc.), aromatic hydrocarbons (benzene, toluene, xylene, ethylbenzene, methylnaphthalene, phenyl xylyl ethane, etc.), nitriles (acetonitrile, isobutylonitrile, etc.), acid amides (N,N-dimethylforMamide, N,N-dimethylacetamide, etc.), and dimethylsulfoxide, vegetable oils (soy bean oil, cottonseed oil, etc.). Examples of the gaseous carriers include CFC gases, butane gas, LPG (liquefied petroleum gas), and dimethyl ether, carbon dioxide gas.

The surfactant includes, for example, alkyl sulfate salts; alkylsulfonates, alkylarylsulfonates, alkyl aryl ethers and their polyoxyethylene adducts, polyethylene glycol ethers, polyhydric alcohol esters and sugar alcohol derivatives.

Other auxiliaries for formulation include an adhesive agent, a dispersing reagent, a stabilizer, and others, and examples thereof include casein, gelatin, polysaccharides (starch, gum arabic, cellulose derivative, alginic acid, etc.), lignin derivatives; bentonite, synthetic water-soluble polymers (polyvinylalcohol, polyvinylpyrrolidone), polyacrylic acid, BHT (2,6-di-tert-butyl-4-methylphenol), and BHA (mixture of 2-tert-butyl-4-methoxyphenol and 3-tert-butyl-4-methoxyphenol).

The base material of the insecticide coil is, for example, a mixture of a vegetable powder such as wood powder or sake lees powder and a binder such as tabu powder (powdered leaves of the *Machilus thunbergii* tree), starch, or gluten.

The base material for the insect electrocuting mat is, for example, a cotton linter molded into the plate shape, or a molding of a mixed fibril of cotton linter and pulp in the plate shape.

Examples of the base materials for the self-combustion fumigant include combustible heat-generating agents such as nitrate salts, nitrite salts, guanidine salts, potassium chlorate, nitrocellulose, ethylcellulose, and wood powder; thermal decomposition stimulants such as alkali-metal salts, alkali-earth metal salts, dichromate salts, and chromate salts; oxygen-supplying agents such as potassium nitrate; combustion aides such as melamine and wheat starch; fillers such as diatomaceous earth; and binders such as synthetic adhesives.

Examples of the base materials for the chemical-reaction fumigant include heat-generating agents such as alkali metal sulfides, polysulfides, and hydrosulfides and calcium oxide; catalysts such as carbonaceous substances, iron carbide, and activated clay; organic foaming agents such as azo dicarbonamide, benzenesulfonyl hydrazide, dinitropentamethylenetetramine, polystyrene, and polyurethane; and fillers such as natural and synthetic fibrils.

Examples of the base materials for the unheated vaporization agent include thermoplastic resins and papers (filter paper, Japanese paper, etc.).

Examples of the base materials for the poisonous bait include feedstuff components such as grain powder, vegetable oil, saccharides, and crystalline cellulose; antioxidants such as dibutylhydroxytoluene and nordihydroguaiaretic acid; preservatives such as dehydroacetic acid; stimulants for prevention of unintended intake by children or pets such as red pepper powder; and insect-attracting flavors such as of cheese, onion, and peanut oil.

The method for controlling harmful insect according to the present invention is practiced by applying the pesticidal composition according to the present invention to the insect or a locus where the insect inhabits.

The methods for applying the inventive composition or the formulation thereof includes specifically the following methods, and it is selected properly according to the shape, the use site and others of the inventive composition.

(1) Method comprising applying the inventive composition to insects or a locus where the insects inhabits as it is.
(2) Method comprising diluting the inventive composition with a solvent such as water and applying the diluted composition to the insects or a locus where the insects inhabit.

In this case, usually, the formulation of the inventive composition or the preparation, such as an emulsion, a water-dispersible powder, a flowable agent, or a microcapsular formulation, is diluted to a total concentration of the Ester compounds at 0.1 to 10,000 ppm.

(3) Method comprising heating the inventive composition or the formulation thereof and vaporizing the active ingredient therein at the locus where the insects inhabit.

In this case, the dosage and the dosage concentration of the inventive compound can be determined respectively, properly according to the shape, application period, application site, and application method of the inventive composition and also to the kind of the insects, the damage by the insects, and others.

EXAMPLES

Hereinafter, the present invention will be described more in detail with reference to Preparative Examples, Test Examples, and others, but the present invention is not limited to these Examples.

Preparative Examples for the inventive compositions will be described first. "Part" below means "part by weight".

Preparative Example 1

0.00156 part of 4-methoxymethyl-2,3,5,6-tetrafluorobenzyl (Z)-1R-trans-3-(2-cyano-1-propenyl)-2,2-dimethylcyclopropanecarboxylate, 50 parts of propylene glycol monomethyl ether and the balance of deodorant kerosene (Neochiozol (manufactured by Chuokasei Co., Ltd.), initial boiling point: 225° C., dry point: 247° C.) were mixed and agitated at room temperature for 5 minutes, to give 100 parts of a liquid composition (hereinafter, referred to as the inventive composition (1)).

Preparative Example 2

0.00156 part of 4-methoxymethyl-2,3,5,6-tetrafluorobenzyl (Z)-1R-trans-3-(2-cyano-1-propenyl)-2,2-dimethylcyclopropanecarboxylate, 10 parts of propylene glycol monomethyl ether and the balance of deodorant kerosene (Neochiozol (manufactured by Chuokasei Co., Ltd.), initial boiling point: 225° C., dry point: 247° C.) were mixed and agitated at room temperature for 5 minutes, to give 100 parts of a liquid composition (hereinafter, referred to as the inventive composition (2)).

Preparative Example 3

0.00156 part of 4-methoxymethyl-2,3,5,6-tetrafluorobenzyl (Z)-1R-trans-3-(2-cyano-1-propenyl)-2,2-dimethylcyclopropanecarboxylate, 10 parts of propylene glycol monoethyl ether and the balance of deodorant kerosene (Neochiozol (manufactured by Chuokasei Co., Ltd.), initial boiling point: 225° C., dry point: 247° C.) were mixed and agitated at room temperature for 5 minutes, to give 100 parts of a liquid composition (hereinafter, referred to as the inventive composition (3)).

Preparative Example 4

0.00156 part of 4-methoxymethyl-2,3,5,6-tetrafluorobenzyl (Z)-1R-trans-3-(2-cyano-1-propenyl)-2,2-dimethyicyclopropanecarboxylate, 10 parts of dipropylene glycol monomethyl ether and the balance of deodorant kerosene (Neochiozol (manufactured by Chuokasei Co., Ltd.), initial boiling point: 225° C., dry point: 247° C.) are mixed and agitated at room temperature for 5 minutes, to give 100 parts of a liquid composition.

Hereinafter, preparation of comparative liquid compositions is described in the following Comparative Preparative Examples.

Reference Preparative Example 1

0.00156 part of 4-methoxymethyl-2,3,5,6-tetrafluorobenzyl (Z)-1R-trans-3-(2-cyano-1-propenyl)-2,2-dimethylcyclopropanecarboxylate, 50 parts of dichloromethane and the balance of deodorant kerosene (Neochiozol (manufactured by Chuokasei Co., Ltd.), initial boiling point: 225° C., dry point: 247° C.) were mixed and agitated at room temperature for 5 minutes, to give 100 parts of a liquid composition (hereinafter, referred to as the comparative composition (1)).

Reference Preparative Example 2

0.00156 part of 4-methoxymethyl-2,3,5,6-tetrafluorobenzyl (Z)-(1R)-trans-3-(2-cyano-1-propenyl)-2,2-dimethylcyclopropanecarboxylate, 10 parts of dichloromethane and the balance of deodorant kerosene (Neochiozol (manufactured by Chuokasei Co., Ltd.), initial boiling point: 225° C., dry point: 247° C.) were mixed and agitated at room temperature for 5 minutes, to give 100 parts of a liquid composition (hereinafter, referred to as the comparative composition (2)).

Hereinafter, Test Examples of the pesticidal effect of the inventive compositions will be described.

Test Example 1

Ten cockroaches *Blattella germanica* (5 males and 5 females) were released in a test container with butter applied on the internal wall (diameter 8.75 cm, height 7.5 cm, bottom face: 16 mesh metal gauze). The container was placed on the bottom of the test chamber (bottom face: 46 cm×46 cm, height: 70 cm). 1.5 g of the inventive composition (1) was sprayed with a spray gun from a height of 60 cm above the container top face (spray pressure: 0.4 kg/cm$^2$). 30 minutes after spraying, the container was removed from the test chamber. The cockroaches *Blattella germanica* were collected from the container, placed in a clean polyethylene cup (bottom face diameter 8.2 cm), fed with food and water, and left still at room temperature while the container was covered with a cap having an ventilation hole. In three days, the mortality of the cockroaches was determined (average of duplicate).

The same procedures were repeated except for using the comparative composition (1) in place of the inventive composition (1) to determine the mortality (average of duplicate).

The results are summarized in Table 1.

TABLE 1

|  | Mortality (%) |
| --- | --- |
| Inventive composition (1) | 60 |
| Comparative composition (1) | 10 |

Test Example 2

Ten cockroaches Blattella germanica (5 males and 5 females) were released in a test container with butter applied on the internal wall (diameter 8.75 cm, height 7.5 cm, bottom face: 16 mesh metal gauze). The container was placed on the bottom of the test chamber (bottom face: 46 cm×46 cm, height: 70 cm). 1.5 g of the inventive composition (2) was sprayed with a spray gun from a height of 60 cm above the container top face (spray pressure: 0.4 kg/cm$^2$). 30 minutes after spraying, the container was removed from the test chamber. The cockroaches Blattella germanica were collected from the container, placed in a clean polyethylene cup (bottom face diameter 8.2 cm), fed with food and water, and left still at room temperature while the container was covered with a cap having an ventilation hole. In three days, the mortality of the cockroaches was determined (average of duplicate).

The same procedures were repeated except for using each of the inventive composition (3) and the comparative composition (2) in place of the inventive composition (2) to determine the mortality (average of duplicate).

The results are summarized in Table 2.

TABLE 2

|  | Mortality (%) |
| --- | --- |
| Inventive composition (2) | 60 |
| Inventive composition (3) | 70 |
| Comparative composition (2) | 20 |

The invention claimed is:

1. A pesticidal composition, comprising:
   4-methoxymethyl-2,3,5,6-tetrafluorobenzyl 3(2-cyano-1-propenyl)-2,2-dimethylcyclo-propanecarboxylate;
   a saturated hydrocarbon having an initial boiling point of 150° C. or higher and a 95%-distillation temperature of 300° C. or lower; and
   at least one glycol ether selected from the group consisting of mono-($C_2$-$C_3$)-alkylene glycol mono-($C_1$-$C_3$)alkylethers and di-($C_2C_3$)-alkylene glycol mono-($C_1$-$C_3$)-alkyl ethers.

2. The pesticidal composition according to claim 1, wherein the composition comprises the saturated hydrocarbon in an amount of 0.5 to 10 parts by weight per part by weight of the glycol ether.

3. The pesticidal composition according to claim 1 or 2, wherein the composition comprises 4-methoxymethyl-2,3,5,6-tetrafluorobenzyl 3-(2-cyano-1-propenyl)-2,2-dimethylcyclopropanecarboxylate in an amount of 0.00001 to 0.1 part by weight per part by weight of the glycol ether.

4. The pesticidal composition according to claim 1, wherein the composition comprises 4-methoxymethyl-2,3,5,6-tetrafluorobenzyl 3-(2-cyano-1-propenyl)-2,2-dimethylcyclopropanecarboxylate in an amount of 0.0001 to 0.5% by weight.

5. The pesticidal composition according to claim 1, wherein the glycol ether is one or two glycol ethers selected from the group consisting of propylene glycol monomethyl ether and propylene glycol monoethyl ether.

6. The pesticidal composition according to claim 1, wherein the composition is for controlling insects Blattaria.

7. A pest-controlling agent, comprising the pesticidal composition according to claim 1.

8. A method for controlling harmful insect comprising applying an effective amount of a pesticidal composition comprising: 4-methoxymethyl-2,3,5,6-tetrafluorobenzyl 3-(2-cyano-1-propenyl)-2,2-dimethylcyclopropanecarboxylate; a saturated hydrocarbon having an initial boiling point of 150° C. or higher and a 95%-distillation temperature of 300° C. or lower; and at least one glycol ether selected from the group consisting of mono-($C_2$-$C_3$)-alkylene glycol mono-($C_1C_3$)alkylethers and di-($C_2C_3$)-alkylene glycol mono-($C_1$-$C_3$)-alkyl ethers to the insect or a locus where the insect inhabits.

9. The method according to claim 8, wherein the composition comprises the saturated hydrocarbon in an amount of 0.5 to 10 parts by weight per part by weight of the glycol ether.

10. The method according to claim 8 or 9, wherein the composition comprises 4-methoxymethyl-2,3,5,6-tetrafluorobenzyl 3-(2-cyano-1-propenyl)-2,2-dimethylcyclopropane-carboxylate in an amount of 0.00001 to 0.1 part by weight per part by weight of the glycol ether.

11. The method according to claim 8, wherein the composition comprises 4-methoxymethyl-2,3,5,6-tetrafluorobenzyl 3-(2-cyano-1-propenyl)-2,2-dimethyl cyclopropanecarboxylate in an amount of 0.0001 to 0.5% by weight.

12. The method according to claim 8, wherein the glycol ether is one or two glycol ethers selected from the group consisting of propylene glycol monomethyl ether and propylene glycol monoethyl ether.

13. The method according to claim 8, wherein the composition is for controlling insects Blattaria.

* * * * *